United States Patent
Sinclair

(10) Patent No.: US 7,910,599 B2
(45) Date of Patent: Mar. 22, 2011

(54) METHOD FOR TREATING EATING DISORDERS BY SELECTIVE EXTINCTION WITH TRANSDERMAL NALOXONE

(76) Inventor: John David Sinclair, Espoo (FI)

( * ) Notice: Subject to any disclaimer, the term of this patent is extended or adjusted under 35 U.S.C. 154(b) by 1595 days.

(21) Appl. No.: 11/031,534

(22) Filed: Jan. 10, 2005

(65) Prior Publication Data

US 2006/0154946 A1     Jul. 13, 2006

(51) Int. Cl.
*A01N 43/42*     (2006.01)
*A61K 31/44*     (2006.01)
*C07D 489/08*     (2006.01)

(52) U.S. Cl. .......................................... 514/282; 546/46
(58) Field of Classification Search .................. 514/277, 514/337, 345, 909, 910, 282; 546/46
See application file for complete search history.

(56) References Cited

U.S. PATENT DOCUMENTS 4,626,539 A * 12/1986 Aungst et al. ................. 514/282
6,569,449 B1    5/2003 Stinchcomb et al. ......... 424/449

OTHER PUBLICATIONS

Raymond, N.; Zwaan, M.; Mitchell, J.; Ackard, D; Thuras, P. "Effect of a Very Low Calorie Diet on the Diagnositic Category of Individuals with Binge Eating Disorder", Jan. 2002, International Journal of Eating Disorders, 31(1), 49-56.*
Fairburn, C.G.; Wilson, G.T. "Binge Eating: Nature, Assessment, and Treatment", 1993, Chapter 1, p. 9.*
Fichter, M.M., "Die medilcamentöse Behandlung von Anorexia and Bulimia nervosa," *Nervenarzt*, vol. 64, No. 1, pp. 21-35, (1993).
Drewnowski, Adam et al., "Naloxone, an opiate blocker, reduces the consumption of sweet high-fat foods in obese and lean female binge eaters," *The American Journal of Clinical Nutrition*, vol. 61, No. 6, pp. 1206-1212, (1995).
"Drug treatment for binge-eating disorders", *Journal of the American Dietetic Association*, vol. 95, No. 11, p. 1329, (1995).

* cited by examiner

*Primary Examiner* — Sreeni Padmanabhan
*Assistant Examiner* — Kendra D Carter
(74) *Attorney, Agent, or Firm* — Kubovcik & Kubovcik

(57) ABSTRACT

A method for treating eating disorders by repeatedly administering naloxone in a dosage sufficient to block the effects of opiate agonists to a subject suffering from an eating disorder caused by one or more related problem responses; while the amount of naloxone in the subject's body is sufficient to block opiate effects, having the subject make one of the problem responses from which the subject suffers in the presence of stimuli similar to those to which it had been learned, after the amount of naloxone is no longer sufficient to block opiate effects, having the subject make healthy eating responses to food items that do not trigger the problem responses; and continuing the steps of administration of naloxone and having one after another of the problem responses made, followed by having a naloxone-free period in which healthy eating occurs, until the problem responses are extinguished.

7 Claims, 1 Drawing Sheet

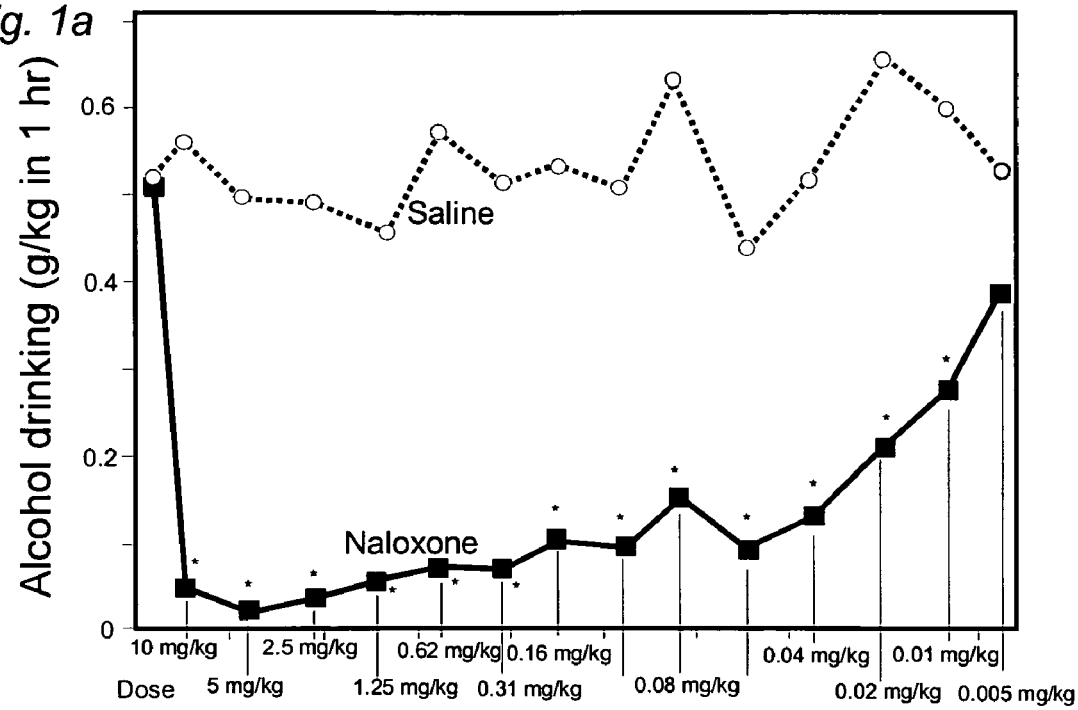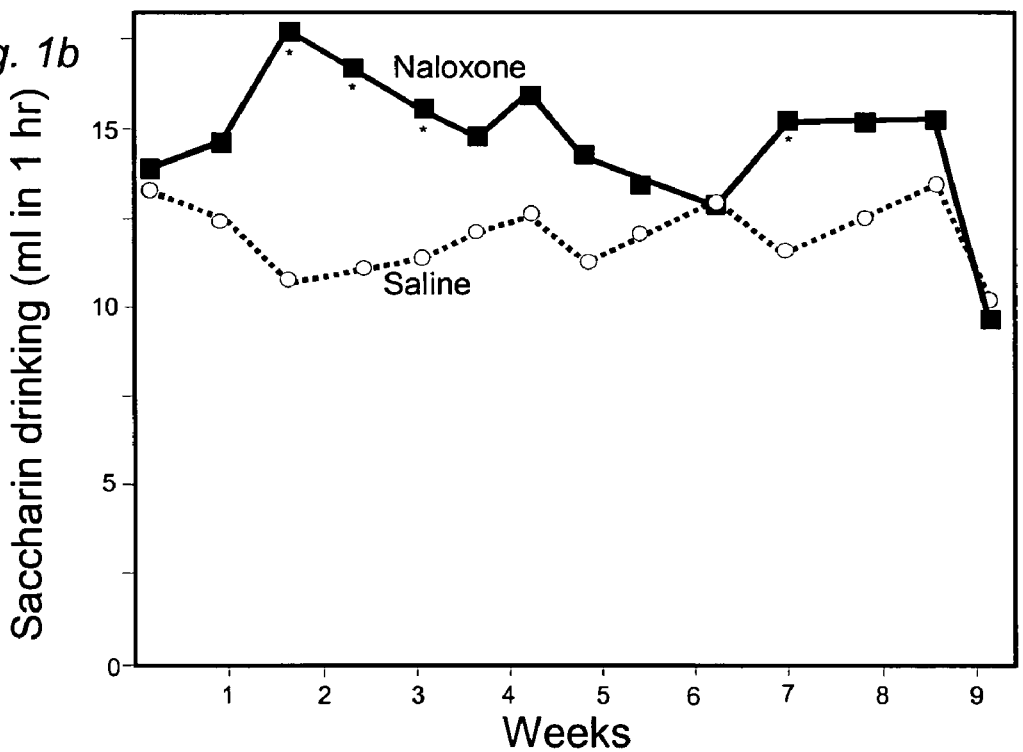

METHOD FOR TREATING EATING DISORDERS BY SELECTIVE EXTINCTION WITH TRANSDERMAL NALOXONE

BACKGROUND FROM TREATING ADDICTIONS

Opioid antagonists have been patented for inducing anorexia (Smith, U.S. Pat. No. 4,217,353, 1980; U.S. Pat. No. 4,477,457, 1984), and they also have been patented for treating anorexia (Huebner, U.S. Pat. No. 4,546,103, 1985). Both results are valid. The antagonists can also reduce binge eating and also the purging associated with bulimia, but normal eating, too. Narrowly limited experiments have found evidence for each of these effects. When put into long term practice, however, the different effects counteract each other and cause complications. For example, as Smith pointed out, the only clinical trial using naloxone for anorexia was inconclusive because they coupled the treatment with giving a hypercaloric diet (Moore et al., 1981).

Unfortunately, the methods used and previously proposed for the treatment of eating disorders are unable to separate these various actions. Consequently, the antagonists have produced mixed clinical results, have not received FDA approval for use with eating disorders, and currently are not being used clinically for such purposes.

In contrast, in the field of alcoholism and drug addiction treatment, I proposed a method in which the antagonists specifically remove the addictive behavior (Sinclair, U.S. Pat. No. 4,882,335, Nov. 21, 1989; U.S. Pat. No. 5,587,381, Dec. 24, 1996). Our double-blind placebo-controlled clinical trial has shown naltrexone is effective when used in accord with this method but not when use otherwise (Heinälä et al., 2001). Similar results have been obtained in nearly all trials (Sinclair, 2001). Naltrexone has been approved by the FDA for use in alcoholism treatment. Going one step further, I improved the method into a procedure of "selective extinction" that not only removes alcoholism and drug addiction but also enhances other competing behaviors (Sinclair, U.S. Pat. No. 5,587,381, 1996; Sinclair et al., 1994; Sinclair, 2001). Especially here in Finland where naltrexone is used in this selective manner, it has become a major factor in the treatment of alcoholism.

The present invention takes this selective extinction method for separating the actions of opioid antagonists on different behaviors and contemplates applying it to the treatment of eating disorders. In addition, several innovations are proposed to optimize the method to the eating disorder field and which then differentiate the method from all previously proposed treatments.

The key for how to separate the actions of the antagonists comes from an understanding of how the antagonists act in the nervous system to produce benefits.

There are two basic processes through which long-term change is made in the organization of the nervous system as a result of experience: one causes learning by strengthening synapses; the other causes habituation and extinction by weakening synapses (see Sinclair, 1981). Experimental results also show that the two occur under different circumstances and follow different rules. Thus, extinction is not simply learning to do something else but rather a separate phenomenon. It also is distinct from forgetting; it is an active process for removing unsuccessful responses and requires the emission of the response in the absence reinforcement.

Our preclinical experimental results had shown that alcohol drinking is a learned behavior (Sinclair, 1974), and that opioid antagonists suppress alcohol drinking by mechanism of extinction (Sinclair, U.S. Pat. No. 4,882,335, Nov. 21, 1989; Sinclair, 1990). Extinction weakens only those responses that are made while reinforcement is blocked. There the method I proposed for treating alcoholism had the antagonist being administered just before the alcoholic drank alcohol.

Others in the field, however, believed that opioid antagonists block the craving for alcohol caused by an imbalance, either a deficiency in opioid receptor activity (Tractenberg and Blum, 1987; Volpicelli et al., 1990) or having too much opioid receptor activity (Reid and Hubbell, 1922). According to these theories, the antagonists would be effective if given during abstinence; they would block craving and the onset of drinking.

Our preclinical experiments had shown that giving opioid antagonists during abstinence not only failed to reduce subsequent drinking, but actually tended to increase subsequent drinking above control levels (Sinclair et al., 2003). The same result was found in our dual clinical trial (Heinola et al., 2001). Naltrexone was effective when paired with alcohol drinking, but naltrexone tended to be worse than placebo when given during abstinence. Similar results can be seen in the other clinical trials (Sinclair, 2001). The latest published count had 41 clinical trials that obtained significant results from using opioid antagonists in a manner allowing extinction; 37 trials using the antagonists in ways precluding extinction, however, got negative results; only 4 trials had results contrary to this conclusion (Fantozzi and Sinclair, 2004).

The mechanism causing the increase in alcohol drinking when antagonists are administered only during abstinence can be used to improve the efficacy of treatment. It can increase the strength of behaviors other than alcohol drinking, of behaviors that can compete with drinking and help fill the vacuum as drinking is extinguished. At the same time other behaviors that are reinforced by endorphins are protected from extinction. One problem noted in some of the clinical alcohol trials is a reduction in the patients' interest in sweets or carbohydrates, or in sex (Bohn et al. 1994; Balldin et al., 1997) This is probably caused by these behaviors being made while on naltrexone and thus, along with alcohol drinking, being partially extinguished. Naltrexone given to humans reduces their preference for saccharin (Arbisi et al., 1999)

The first step in our clinical use of selective extinction in alcoholism treatment is to have patients make a list of behaviors they find pleasurable. The clinician identifies the behaviors on the list that are probably reinforced by the opioidergic system and advises the patient to avoid engaging in these activities on the days when taking naltrexone and drinking. In the beginning of treatment, this is essentially every day.

After the treatment has reduced craving for alcohol, usually during the first month, the patient is advised to have a weekend, starting with Friday evening, with no naltrexone and drinking. Friday night and Saturday constitute a wash-out period for naltrexone to be removed from the body. On Sunday afternoon, the patient chooses some of the opioidergically-reinforced behaviors: eating a highly palatable meal, jogging, having sex, cuddling, cards, etc. As expected, patients usually report that the activities at this time are unusually enjoyable.

The patients can return to naltrexone and drinking on Monday. They are advised, however, to try the next week to have a longer period without naltrexone and drinking but with the alternative behaviors. A three-year follow-up showed that complying patients reported a maximum of 1.5±0.4 (SEM) days per week (Sinclair et al., 2000).

The example included here is a prior preclinical experiment in which the alternative opioidergically-reinforced behavior was saccharin drinking. Alcohol experienced rats had continual access to food and water. Alcohol solution was available for only an hour a day for 2 to 4 days. On the next day or two, saccharin solution instead was available. Naloxone (or saline for the control group) was injected prior to the alcohol session. During the first three weeks when the naloxone doses were in the range previously found to be effective, the alcohol drinking was practically abolished. Saccharin drinking in the same animals was significantly increased.

BACKGROUND FOR EATING DISORDERS

The opioidergic system reinforces responses, not only when activated by an opiate or alcohol, but also when certain types of stimuli are experienced. The stimuli cause a release of opioids in the brain, reinforcing the responses that produced these stimuli. Consequently, opioid antagonists have been shown in clinical trials to be effective in treating compulsive gambling (Kim, U.S. Pat. No. 5,780,479, 1998; Kim et al., 2001).

Opioidergic reinforcement is well documented for food-related stimuli. On the basis of a large body of data, Cooper and Kirkham (1990, p. 91) concluded that "ingested items provide stimuli which lead to the release of endogenous opioidergic peptides in the central nervous system". The system does not appear to be involved in the reinforcement from eventually obtaining calories, but rather with that from the pleasant stimulation. For example, opiate antagonists reduce sham feeding of sucrose, and they suppress the eating of chocolate-coated cookies by rats, but not the intake of normal rat chow. Similarly in humans, the antagonist nalmefene suppresses intake of highly palatable foods but not that of less pleasant tasting ones. Another general finding is that antagonists suppress food consumption (and alcohol drinking) only in the later parts of the first session or eating binge but not at the beginning.

Other workers in the field interpret these results differently than 1 do. They suggest that "endogenous opioids play a central role in the modulation of appetite" (Jonas, 1990). The opioids released by food-related stimuli block satiety effects and make food stimuli continue to be pleasant even after caloric needs have been satisfied; thus the opioid release "contributes to the maintenance of ingestional behavior" (Cooper and Kirkham, 1990) and is "involved with processes associated with continuance of eating rather than starting to eat" (Wild and Reid, 1990). In some people the opioid release is too large or too long, and thus they do not stop eating (or alcohol drinking) normally but rather have "out of control" binges. An opiate antagonist blocks this opioid action; therefore, so long as the antagonist is present the duration of a binge is shortened. Similarly with alcohol drinking, "antagonists at opioceptors [sic] would reduce the propensity to continue to drink once drinking has begun" (Hubbell and Reid, 1990). Another interpretation was made by Huebner (U.S. Pat. No. 4,546,103, 1985). He saw endorphins providing satisfaction and pleasure from purging for bulimic patients and from anorexic behavior. Blocking the opioid system with endorphins would remove the reason for patients making the behaviors, and thus help them to stop.

Both of these interpretations are best served by continual opioid blockade. If endorphins cause normal eating to expand to a binge, then continual blockade would continually prevent binges. Or if endorphins provide the pleasure from purging, continual naltrexone would suppress purging at all times. No one previously has proposed using only short periods of blockade interspersed with periods when the opioid system was functional, as is done in the present invention.

I see the results not as immediate effects of the opioids and the antagonists on appetite or satiety, but rather as aftereffects produced by learning and extinction. When a highly palatable food is consumed, opioids are released and as a result, after consolidation, the response is stronger. In some people the responses are reinforced so often and so well that they become extremely strong and cannot be controlled properly. When the response is emitted while an opiate antagonist blocks the reinforcement, the response is weakened. The effect can be seen even during the first session, not at the very beginning but reducing intake in the latter portions and thus terminating a binge earlier. The antagonists can reduce purging if the behavior is emitted while reinforcement is blocked because of extinction.

Opiate antagonists have been tested for eating disorders but the methods used were ones that would be appropriate if the antagonists worked by directly increasing satiety or reducing appetite. In particular, the subjects were kept continually on the antagonists in order to prevent all eating from getting out of control and turning into a binge. For example, Alger et al. (1990) gave patients suffering from binge eating initially 50 mg of the longer lasting antagonist, naltrexone, once daily, then twice daily, and if that did not work, 3 times daily, apparently for the purpose of making sure the patient was never free of naltrexone. Although some patients seemed to benefit, over all the naltrexone treatment was not significantly better than placebo. Similarly, although some uncontrolled studies found benefits from naltrexone in the treatment of bulimia, the one placebo-controlled study did not (Jonas, 1990). A recent review of pharmacological treatments for binge eating does not include opioid antagonists among the medicines for which there is clinical support (Carter et al., 2003).

According to the extinction hypothesis, keeping a person continually on the antagonist is not optimal for treating eating disorders. In the case of binge eating, it weakens not only the binge-eating response but also all other emitted responses reinforced through the opioidergic system. This makes the procedure less effective because the probability of binge-eating is determined not by its absolute strength but rather by its strength relative to all competing responses. Of particular importance, eating in a healthy manner is also extinguished.

The present invention instead employs the "selective extinction" procedure (Sinclair, U.S. Pat. No. 5,587,381, 1996) which has the person take an antagonist only before making the problem response but free of the antagonist at times when the problem response is not made. Thus extinction sessions, when mainly the problem response is weakened, are interspersed with "learning periods" when other competing response including healthy eating responses can regain their strength. In the treatment of bulimia, only binge-eating of specific highly palatable food is weakened, but other competing responses are not.

Experimental support comes from my studies with alcohol drinking: keeping rats continually on an antagonist (large doses of naltrexone or nalmefene in the food) significantly lowered alcohol drinking but did not reduce it as much did selective extinction produced by 1 hour sessions daily when alcohol and the short-acting antagonist, naloxone, were present, as shown in the example here.

Support may also be seen in the fact that the only blind, placebo-controlled experiment with humans to obtain significant results involving binge eating and antagonists was an acute study in which naloxone significantly reduced the size of an eating binge (Atkinson, 1982).

There are two other advantages of selective extinction. First, the continual presence of an antagonist produces upregulation of opioid receptors (Unterwald and Zukin, 1990; Parkes and Sinclair, 2000). Consequently, a problem response would produce more reinforcement after the end of antagonist treatment, than it did before. Up-regulation should be attenuated with the selective extinction procedure because the antagonist is present only for relative short sessions interspersed with antagonist-free periods.

Second, although opiate antagonists are considered safe, there are side-effects, such as liver toxicity with naltrexone, elevated cortisol levels, and possible immunosuppressive effects (Morgan and Kosten, 1990). These side-effects should be greatly reduced or eliminated with only periodic administration of the antagonist. The dysphoria sometimes reported with continual administration might also be caused by the general blocking of pleasure from a wide range of activities, and should be less of a problem with selective extinction where the person is free to enjoy opioidergic reinforcement from other responses during the learning periods.

Selective extinction can be used for treating a variety of eating disorders. In addition to bulimia and binge-eating, it could be used as a dieting aid. A contributing factor to obesity for many people is overly-strong eating responses and cravings for a few highly palatable and high-energy foods: chocolate, cookies, peanut butter, etc. Losing weight and then maintaining a normal weight would be possible after these specific responses were removed by selective extinction. Similarly, selective extinction could be used by people who are not necessarily over-weight but have to restrict their intake of a particular substance (e.g., sugar or sodium chloride) that can be identified with a specific stimulus that activates the opioidergic system. (There is evidence that both sweet and salty tastes are reinforcing through this system (Levine et al., 1982).)

The present invention takes advantage of a relationship between opiate antagonists and a phenomenon I discovered called the "alcohol-deprivation effects". Taking alcohol away after prolonged prior experience gradually over several days increases the desire for it. When it is first returned, intense drinking begins immediately, probably accompanied by intensified pleasure and reinforcement. Deprivation effects also develop for saccharin and specific highly-palatable foods, as well as for many habitual behaviors. Opiate antagonists have been found to be more effective in suppressing alcohol drinking after deprivation (Kornet et al., 1990). The probable reason is that extinction (unlike learning) is most effective with "massed trials", i.e., when the response is made over and over again, vigorously, without pausing (see Sinclair, 1981). Therefore, the extinction of specific eating responses will generally be done after several days of deprivation of the specific food item. For example, if chocolate ice cream is listed by patients as a triggering food for bulimia, these patients will be told to abstain from eating chocolate ice cream, plus ice cream in general and chocolate in general, for a week before taking an opioid antagonists and getting unlimited chocolate ice cream to eat and purge.

There is evidence linking anorexia nervosa to the opioidergic system. First, it may develop from bulimia (Kassett and Gwirtsman, 1988). Second, there is some preliminary evidence from a small study showing for improvement of anorexia nervosa from treatment with an opiate antagonist (Luby et al., 1987). Marrazzi and Luby (1986) suggested that starvation causes the release of endorphins; anorexic patients starve themselves supposedly to get elation from their own opioids. I suspect the situation is somewhat more complicated. The specific anorexic behaviors may be reinforced by the opioid system, but a major factor contributing to the condition is the extinction of normal eating response. During the developmental phase, the patients make all of the normal eating responses: going to the table, taking the food, pushing it around with a fork, but then willfully withholding the responses of tasting and swallowing the food. Thus the preliminary responses are made but do not get reinforcement from taste or from removal of hunger, and as a result are extinguished. In any case, it is clear that the solution is a strengthening of normal eating behaviors, and extinction of the responses maintaining anorexia. This should be accomplished by administering opioid antagonists while the patient is not eating, interspersed with antagonist-free periods when the patient does in fact eat a small amount of highly palatable food Extinguished responses can be relearned; indeed they are relearned more readily than they were learned the first time. Subjects can be advised after a given period of treatment to refrain henceforth from making the extinguished response ever again in order to avoid relearning, but they cannot avoid all responses reinforced through the opioidergic system. One solution, used in alcoholism treatment, is to continue taking antagonist indefinitely whenever there is a risk of drinking, or in this case of making the eating disorder response again. Alternatively, selective extinction can be used to "trim" offending responses that are beginning to arise again before they become harmfully strong. Like finger-nails, the growth of responses is a useful natural process but can become harmful when left uncontrolled. Thus individuals with a predilection for developing overly-strong responses might periodically review their current activities and then trim those responses that were beginning to get too strong—as casually and almost as easily as we trim our nails.

TECHNICAL INNOVATIONS

Perhaps the greatest technological quest in this field since the discovery of the opioid antagonists has been for preparations that would cause the antagonists to remain in the body for longer periods of time. Naltrexone and nalmefene have been preferred over naloxone not only because they can be taken orally but also because of their much longer half-lives. Various slow-release methods for naltrexone and nalmefene have been developed over the passed two decades to provide weeks or months of constant blockade.

This quest is consistent with the previously proposed methods for treating bulimia and binge eating with opioid antagonists. Their imagined mechanisms of action would work best if the antagonists were always present, thus eliminating supposed problems of patient compliance.

The present invention, however, contemplates alternating periods when an opioid antagonist blocks the opioid system (during which the eating disorder behaviors are emitted) with periods when the patient's body is free of antagonist (during which normal healthy eating behaviors are made).

We have used a similar "selective extinction" procedure extensively in treating alcoholism (Sinclair, 2001). (Incidentally, there has been little problem here with compliance. Alcoholics have difficulty complying if you tell them to refrain from drinking. They do not have a problem, however, with obeying the instruction to take a pill always before drinking.)

With alcoholics, we include a wash-out period of about 48 hours for removal of the naltrexone. During this time the patients should not drink alcohol and they also should not engage in the alternative opioidergically-reinforced behaviors that we wish to strengthen. This is not a problem with alcoholism or drug addiction.

In the case of eating disorders, such long wash-out periods are not possible. For example, when treating bulimia, the behavior we wish to extinguish is eating foods that trigger bulimia. The alternative behavior we wish to strengthen is eating foods that do not trigger bulimia. Obviously patients cannot be expected to avoid both activities, that is, to refrain from all eating, for a 48 hour wash-out period. Nalmefene is removed even more slowly.

Naloxone, however, has a half-life of only 30 to 80 minutes in humans. A patient given naloxone on one day would be free of it the following day.

Naloxone is metabolized so rapidly in the liver that all of it is removed during the first pass after oral administration. Consequently, it usually is injected, as was the case in a previous test for treating anorexia (Huebner, U.S. Pat. No. 4,546,103, 1985).

Transdermal administration of naloxone, however, is much better suited for repeated self-administration. I previously proposed a transdermal devise for administering a fixed dose of an opioid antagonist, including naloxone, for use in alcoholism treatment (Sinclair, U.S. Pat. No. 5,096,715, 1992). Recent experiments (Panchagnula et al., 2001) have shown this devise with 33% propylene glycol as the vehicle and ethanol as the permeation enhancer is even more effective for transdermal delivery of naloxone than 1 had anticipated: "theoretically blood levels well above the therapeutic concentration of naloxone can be achieved" with a transdermal patch of a convenient size. An intranasal spray has also been shown suitable for rapid administration of naloxone for the majority of subjects and could also be used, probably in combination with transdermal administration (Loimer et al., 1992).

Avoiding the oral route also has distinct advantages for selective extinction of eating disorders. First, there is the problem that some of an orally administered medication would be lost by purging, or not taken by anorexic patients. Second, troubles with the gastrointestinal tract are common complications with eating disorders. Oral administration itself irritates the throat and it directs the highest concentration of the medication to intestines where it interacts with opioidergically controlled motility. Third, the response of taking an oral medication is similar to the eating responses we are trying to alter with the treatment, thus adding a possible complication to the procedure.

SUMMARY OF THE INVENTION

The lifetime prevalence of bulimia is 2.8% for women, and 5.7% of women will show bulimia-like syndromes (Kendler et al., 1992). The disorder was strongly influence by genetics, with a heritability coefficient of 55%. Comorbidity was reported between bulimia and anorexia nervosa, alcoholism, panic disorder, generalized anxiety disorder, phobia, and major depression.

The present invention contemplates a therapeutic method, utilizing the ability of opiate antagonist to block positive reinforcement from stimuli produced by highly-palatable foods, from purging, and from anorexic behavior in order to extinguish bulimia and other eating disorders while simultaneously strengthening normal healthy eating behaviors and the consumption of foods conducive to health.

The subject suffering from one of these overly-strong eating disorder responses makes the response repeatedly, in the presence of stimuli similar to those to which the response had been learned, while active quantities of naloxone are in his or her brain, thus eventually extinguishing the response and removing the desire to make the response. These extinction sessions are separated by "learning periods" when the subject is free of antagonist and can make other responses but not the problem response, in order to restore the strength of competing responses. Thus the problem response is selectively extinguished.

In most cases the subject will suffer from several related problem responses: e.g., overly-strong eating responses for a dozen specific highly palatable food items. Each will be extinguished separately. Furthermore, prior to extinguishing a particular response, the subject will not be allowed to make that response for at least a week. The resulting "deprivation effect" will assure that the subject is highly motivated to make that response at the beginning of extinction and will increase the effectiveness of extinction.

Depending upon the severity and nature of the problem responses, provisions are made for using the method within a treatment center, as an out-patient treatment, and as a combination of the two.

BRIEF DESCRIPTION OF DRAWINGS

Selective extinction (interspersing periods when alcohol was drunk daily following naloxone injection with periods when saccharin was drunk with no injection) strongly reduced alcohol drinking (FIG. 1a) while increasing saccharin drinking (FIG. 1b) in the same animals relative to intakes by control animals injected with saline. Each data point is the mean of 1 to 4 days. The extremely low doses used from week 4 on have not previously been found to be effective. *$p<0.05$ relative to saline controls.

DESCRIPTION OF PREFERRED EMBODIMENTS

The selective extinction method here can be used with subjects diagnosed as suffering from maladaptive overly-strong responses reinforced by stimulation-induced release of opioids and resulting in eating disorders. It cannot be used for patients for whom the opiate antagonist is contraindicated. In particularly, patients who are physiologically dependent upon opiates must be excluded.

Specific details for the use of selective extinction with each of the different varieties of problem responses are presented below. The initial steps, however, in each case are similar. First, detailed information is obtained about the patient's responses: the particular responses that cause the patient problems, the situations in which they have typically been emitted, and particularly the foods that trigger the behavior. Second, the patient is checked for alcoholism, drug addiction, or other contraindications. Third, if there is any possibility of an active opiate addiction despite denials by the patient, a small dose of opiate antagonist is administered under close medical supervision.

Binge-eating and Bulimia

Severe cases should be handled initially in a treatment center to assure compliance, to increase motivation, to monitor health, and to provide counseling and training concerning correct eating habits. The information obtained includes a list of the patient's "trigger foods", i.e., those highly palatable foods that precipitate binges, are frequently included in binges, are greatly craved, or give the patient intense pleasure when the first bite is eaten. A list is also prepared for the patient of "healthy foods", i.e., nutritious foods that do meet any of the above characteristics for trigger foods.

The patient is kept initially on diet specifically excluding a particular trigger food and foods with similar characteristics for a week prior to treatment. (In the aforementioned example, if the trigger is chocolate ice cream, the patient avoids not only chocolate ice cream but all ice cream and all chocolate.) Naloxone is then administered, perhaps first by nasal spray and then transdermally, and then while active quantities are present in the system, the patient is presented with the trigger food and encouraged to have an eating binge of it. If possible, the situation in which the food is eaten should be similar to that in which the patient usually has had eating binges. The response set should also be similar; e.g., if the patient typically has purged after an eating binge previously, purging should occur also in the extinction session. No healthy foods should be available.

The duration of an extinction session should match the patient's previous binging behavior. If binging normally continued for several days, the same should occur in treatment, with additional transdermal administrations of naloxone being given as needed.

At the end of the extinction session, the transdermal administration is stopped and the skin area involved is washed thoroughly.

The extinction session is followed the next day by a "learning period" of one day or more when no antagonist is given and only healthy foods are available. Not only are trigger foods not available, but also all stimuli related to them; the patient should not see them or smell them, nor should they be discussed in counseling. The safe foods can be restricted to meal times, but the patient can eat as much as desired then: no attempt at dieting should occur during the learning periods. Learning of alternative behaviors can be encouraged, but care should be used with regard to responses reinforced through the opioid system. For example, greater than normal intake of alcohol should not be allowed.)

In subsequent extinction sessions, the patient binges on other trigger foods that have not been included in the previous sessions. In severe case being handled at a clinical center, treatment continues until binge eating with most of the patient's trigger foods has been extinguished and the person has gained greater control over his or her eating habits. Thereafter, an out-patient mode of selective extinction treatment can be used. The subject is given take-home doses of the opiate antagonist and told to take one whenever there is a high probability that unsafe foods will be eaten in the next few hours. The instructions state that the patients should go ahead and have an eating binge if they feel like it, but only after taking naloxone. Under no circumstance should they binge without taking the antagonist. The antagonist should not be taken otherwise, i.e., when the patient thinks there is little chance of eating trigger foods.

Dietary Aid for Stimulus-bound Overeating

An out-patient mode of selective extinction is used for patients with less severe eating problems and high motivation and ability for compliance. It can be used with subjects who are obese or only moderately overweight whose weight problem is not due to glandular anomalies but rather is caused by eating more than more than caloric needs in response to specific stimuli. The stimuli can be specific highly-palatable ("trigger") food items, situations, or moods. Examples of trigger food items would be chocolate, mayonnaise, peanut butter, potato chips, cream, butter, and cheese. Examples of trigger situations are watching television, fast food and other restaurants, parties, holidays, and "midnight snack" excursions. Examples of moods are premenstrual syndrome (PMS), post-traumatic stress (PTS), anxiety in anticipation of a stress situation, and celebration euphoria.

The procedure is the same as that with binge-eating and bulimia except the subject is not kept in a treatment center but rather conducts his or her own extinction sessions in the outside world. The subject is given clear, precise instructions (similar to those specified above for binge eating and bulimia) on how to extinguish the problem eating responses (e.g., 1. create a list of trigger stimuli, 2. choose one, 3 refrain from it for one week, 4. arrange for the trigger stimulus to be present, 5. self-administer naloxone, 6. what to do during intervening "learning periods" when the antagonist is not taken and the trigger stimuli are avoided as much as possible.

Dietary Aid for Limiting Intake of Specific Substances (Sugar, Salt, etc.)

Selective extinction can be used for people who are not necessarily overweight but must reduce their intake of a particular substance that is closely associated with a distinct stimulus that causes opioid release.

One example is with people who need to reduce their intake of sodium chloride. Sodium chloride is closely associated with salty tastes, and there is evidence showing that a salty taste produces reinforcement through the opioidergic system (Levine et al., 1982). The person is given a series of extinction sessions on naloxone and learning periods off of the antagonist. During the extinction sessions a variety of salty-tasting foods are eaten. If necessary, the salty taste could be produced by a salt substitute, but sodium chloride should be used if there is no medical danger from short-term intake of the substance. During the learning sessions, salty-tasting foods are omitted from the diet. The responses of eating salty foods are thus selectively extinguished, while the responses of eating non-salty foods are not weakened and may be enhanced. This will reduce the desire for salty foods and make it easier for the person to stay on a low salt diet.

A similar procedure could be used with people who need to restrict their intake of sugars. Sweet foods are eaten during the extinction sessions and non-sweet ones during the learning periods. The sweet taste could be produced with artificial sweeteners, but sugar should be used if there is no medical danger from such limited intake.

The method also can be used with people who need to restrict their intake of cholesterols or specifically low-density cholesterols. Although there probably is no specific taste stimuli associated with cholesterols, they tend to be present in highest amounts in particular highly-palatable foods. Consequently, during the extinction sessions the person eats these particular foods and during the learning session the person eats foods with low amounts of cholesterol or low-density cholesterols.

This procedure could be used either in a treatment center or on an out-patient basis depending upon the person's ability to comply and the severity of the ailment requiring the dietary limitations.

Anorexia Nervosa

The patient is kept continually on a transdermal opiate antagonist for a period (probably 2 days or more) while intravenous nutrients are supplied. Naltrexone or nalmefene could be used initially but naloxone should be used in the last day.

Antagonist administration is then abruptly terminated. During the next day (a learning period when the system is free of active levels of antagonist), the patient is given small portions of a variety of highly-palatable foods and strongly encouraged to eat at least a small amount. The rebound supersensitivity of the opioid system should help to reinforce the eating responses that are made.

The next day the patient is placed again on the antagonists and fed intravenously. The pattern of extinction sessions and learning periods continues. New highly-palatable foods are introduced on each antagonist-free day, with at least a week between duplication of the same food item in order to allow deprivation effects to increase the reinforcement. After the first sessions, increasing attention is paid to providing a well-rounded, nutritious variety of highly-palatable foods. Pharmacological potentiation of the opioidergic response, e.g., with moderate amounts of alcohol, can be employed.

During extinction session days on the antagonist, the patient is encouraged to make the most common responses from his or her own list of previously-learned competing anorexic responses (e.g., vigorous exercise) that are probably reinforced through the opioid system. In most cases, the aim should be weakening these responses only to a normal level.

EXAMPLE

Male Wistar rats (n=26) were individually housed with daily access to 10% ethanol, with food and water always present. After 2 months prior experience, the rats were switched to having 2-4 alcohol-access days interspersed with 1 or 2 days when saccharin solution (1 g/l) was available for 1 hr. The rats were then divided into 2 matched groups, one always receiving a subcutaneous dose of naloxone prior to alcohol access and a control group receiving a similar injection of saline prior to alcohol access. No injections were made prior to saccharin access. In addition, the naloxone dose was progressively reduced from 10.000 to 0.005 mg/kg.

The naloxone injections significantly reduced alcohol drinking in comparison with both the alcohol intake by the controls and in comparison with their own prior levels (see FIG. 1a). The alcohol drinking continued to be significantly reduced for 8 weeks; many of these weeks involved doses far lower than previously found to be effective. Alcohol drinking was reduced to nearly zero for most rats for 6 weeks. The suppression of drinking of alcohol drinking appears greater than in previous experiments in which both alcohol drinking and antagonist administration occurred every day and specifically greater than in studies aimed at maintaining a continual presence of the antagonist by using longer lasting naltrexone or nalmefene and mixing them with the food.

In contrast to the sharp reduction in alcohol drinking, saccharin drinking increased and eventually was significantly higher than that shown by saline controls (see FIG. 1b). This illustrates a pharmaceutically enhanced learning caused by an increase of reinforcement while the number of opioid receptors remains up regulated from prior treatment with the antagonist.

I claim:

1. A method for treating binge eating by selectively extinguishing the behavior causing binge eating while strengthening normal health eating behaviors, comprising the steps of:
    adminstering naloxone to a subject suffering from binge eating before the subject engages in binge eating behavior;
    and soon after the amount of naloxone ia no longer sufficient to blockopiate effects but while there still is an upregulation of opioid receptors, having the subject make healthy eating responses to food items that do not trigger binge eating for the subject; and
    repeating the steps of administration of naloxone before binge eating behavior is made, followed by having a naloxone-free period in which healthy eating occurs, until the binge eating responses are sufficiently weakened by extinction that the patient can control them.

2. A method for treating bulimia by selectively extinguishing the behavior causing bulimia while strengthening normal health eating behaviors, comprising the steps of:
    administering naloxone to a subject suffering from bulimia before the subject engages in bulimic behavior;
    and soon after the amount of naloxone is no longer sufficient to block opiate effects but while there still is an upregulation of opioid receptors, having the subject make healthy eating responses to food items that do not trigger bulimia for the subject; and
    repeating the steps of administration of naloxone before bulimic behavior is made, followed by having a naloxone-free period in which healthy eating occurs, until the bulimic responses are sufficient weakened by extinction that the patient can control them.

3. A method for treating anorexia nervosa by selectively extinguishing the behavior causing anorexia while strengthening normal health eating behaviors, comprising the steps of:
    administering naloxone to a subject suffering from anorexia nervosa before the subject engages in anorexic behavior;
    and soon after the amount of naloxone is no longer sufficient to block opiate effects but while there still is an upregulation of opioid receptors, having the subject make healthy eating responses; and
    repeating the steps of administration of naloxone while not eating, followed by having a naloxone-free period in which eating occurs, until the anorexic responses are sufficient weakened by extinction and the eating behaviors sufficiently strengthened that the patient can maintain a healthy body weight.

4. A method for treating stimulus-bound overeating by selectively extinguishing the behavior causing overeating while strengthening normal health eating behaviors, comprising the steps of:
    administering naloxone to a subject who habitually overeats in the presence of specific stimuli;
    and while the amount of naloxone in the body is sufficient to block the effects of opiate agonists having the subject overeat in response to those stimuli;
    and soon after the amount of naloxone is no longer sufficient to block opiate effects but while there still is an upregulation of opioid receptors, having the subject make healthy eating responses while the specific stimuli are not present; and
    repeating the steps of administration of naloxone before stimulus-bound overeating behavior is made, followed by having a naloxone-free period in which healthy eating occurs, until the stimulus-bound overeating responses are sufficient weakened by extinction that the patient can control them.

5. A method for helping a subject avoid eating a specific food item as required by a medical condition, by selectively extinguishing the behavior of tasting or eating the specific food item while strengthening other health eating behaviors, comprising the steps of:
    administering naloxone to a subject suffering from a medical condition requiring avoidance of the specific food item before the subject engages in tasting or eating a small amount of the specific food item while the amount of naloxone in the body is sufficient to block the effects of opiate agonists;
    and soon after the amount of naloxone is no longer sufficient to block opiate effects but while there still is an upregulation of opioid receptors, having the subject eat other food items; and
    repeating the steps of administration of naloxone before tasting or eating small amounts of the specific food item, followed by having a naloxone-free period in which eating of other food items occurs, until the responses related to eating the specific food item are sufficient weakened by extinction that the patient can control them.

6. The method in accordance with any one of claims 1 to 5 wherein naloxone is given transdermally and the dose per day is 0.01 to 50 mg.

7. The method in accordance with claim 6 in which the dose of naloxone is started at a high level of 5 to 50 mg and then is progressively reduced over the days of treatment.

* * * * *